United States Patent [19]
Takabu

[11] Patent Number: 6,164,294
[45] Date of Patent: Dec. 26, 2000

[54] MOVABLE DENTAL FLOSS

[76] Inventor: Atsushi Takabu, Yokohama HS-Building,4F 2-9-10, Kitasaiwai, Nishi-ku, Yokohama-shi, Kanagawa-ken, Japan

[21] Appl. No.: 09/434,020

[22] Filed: Nov. 4, 1999

[51] Int. Cl.$^7$ .................................................. A61C 15/00
[52] U.S. Cl. .......................................... 132/327; 132/323
[58] Field of Search ..................................... 132/327, 323, 132/325, 326, 328

[56] References Cited

U.S. PATENT DOCUMENTS

| | | | |
|---|---|---|---|
| 4,790,336 | 12/1988 | Kuo | 132/325 |
| 4,832,062 | 5/1989 | Grollimund et al. | 132/327 |
| 5,183,064 | 2/1993 | Barth | 132/323 |
| 5,197,498 | 3/1993 | Stewart | 132/325 |
| 5,388,600 | 2/1995 | Hart | 132/323 |
| 5,829,458 | 11/1998 | Chodorow | 132/323 |
| 5,931,171 | 8/1999 | Landis et al. | 132/323 |

*Primary Examiner*—Gene Mancene
*Assistant Examiner*—Robyn Kieu Doan
*Attorney, Agent, or Firm*—Antonelli, Terry, Stout & Kraus, LLP

[57] ABSTRACT

A movable dental floss comprises an outer floss tensioning member and an inner floss tensioning member. The outer floss tensioning member and the inner floss tensioning member each have a pair of tensioning levers which face each other and a gripping portion, respectively. The gripping portions are connected, at their respective ends, to each other by a rotatable fixing portion so that one of them is swingable relative to the other. The pairs of the inner and outer floss tensioning levers are curved more at positions farther from respective branch portions thereof in a direction of the relative swing of the gripping portions. The pair of inner floss tensioning levers are rotated relative to the pair of outer floss tensioning levers to let the latter move in a direction of the height of teeth for removing contaminant on and between the teeth.

7 Claims, 5 Drawing Sheets

MOVABLE DENTAL FLOSS

INDUSTRIAL FIELD OF APPLICATION

The present invention relates to a movable dental floss which can suitably remove food pieces, etc. lodged in an interdentium between teeth or a gap between a tooth and the gingiva portion thereof without injuring the gingiva portion, etc., which expels periodontitis bacteria in a periodontal pocket and, moreover, which can be easily and simply used by any person.

PRIOR ART

It is known that if the interdentium between teeth is kept filthy it causes a pyorrhea alveolaris, etc. A periodontitis such as the pyorrhea alveolaris is caused by a gingivitis. The gingivitis is caused by the process in that a bacterial plaque whose nutrient source is dregs, etc. of food in a mouth is formed in a boundary between teeth or the like, which generates sulfide and toxic substances to invade the gingiva. Thus, the gingivitis gives rise to the pyorrhea alveolaris.

Further, the gingiva is liable to be inflamed also in case that food pieces, etc. lodged in a gap of interdentium are left as they are. In order to prevent this, cleaning and training of the gingiva portion have been performed by brushing with a toothbrush However, as to a tooth, its depth is larger than its width and, even as to a foretooth whose depth seems to be smaller than width , its depth is larger than its width at its root. And if a total length of front and rear of whole dental arch is compared with a dimension which is a sum of lengths of left and right depths of each of the teeth, the latter becomes far larger than the former.

Accordingly, by a usual polishing method with the toothbrush, a tip of the brush does not reach into an innermost part of the gap of interdentium between teeth and thus the food pieces, etc. lodged in the innermost part cannot be removed. As a cleaning tool, there is an elongated cylindrical toothpick whose one end potion is made into a conical shape, however, with this toothpick, if its tip is inserted into the gap of interdentium in order to remove the food pieces, etc. contained in the gap of interdentium, the food pieces, etc. are instead pushed into the innermost part of the gap, thereby making it difficult to remove them. If the tip of toothpick is further inserted into the innermost part in order to forcibly remove them, there is a possibility that the gingiva portion is injured.

Besides, the method of cleaning the interdentium using a floss is performed by gripping both ends of the floss and moving fingers or arms. Further, although there is used a floss tensioning tool in which the floss is tensioned in a portion formed in a shape such as V-shape and U-shape and in which a gripping lever is provided, also in this case the cleaning is performed by moving fingers or arms, so that adjustments of its moving width and moving position must be performed by a feel of fingertip.

OBJECT AND SUMMARY OF THE INVENTION

An object of the invention is to provide a movable dental floss in which one floss hitherto used to clean the interdentium between teeth and remove the periodontitis bacteria in the periodontal pocket by moving fingers or arms is made a double floss, and in which the floss is easily moved.

In view of the foregoing problem, as a result of hard study, the invention is one which comprises an outer floss tensioning member and an inner floss tensioning member respectively having floss tensioning means at their tip sides, an outer gripping portion and an inner gripping portion provided at base end sides of the outer floss tensioning member and the inner floss tensioning member, and floss moving means for tensioning a floss in double by superposing the outer floss tensioning member and the inner floss tensioning member and for moving the floss.

Further, the floss tensioning means is constituted by providing the outer floss tensioning member and the inner floss tensioning member respectively with an outer branch portion and an inner branch portion, respectively extending at tip end sides of the outer branch portion and the inner branch portion one pair of outer floss tensioning levers each having an outer floss tensioning groove and one pair of inner floss tensioning levers each having an inner floss tensioning groove, providing an outer floss tensioning stop portion and an inner floss tensioning stop portion on each of upper surfaces of the outer gripping portion and the inner gripping portion, tensioning between the outer floss tensioning grooves and the inner floss tensioning grooves the floss whose both ends are stopped on the outer floss tensioning stop portion and the inner floss tensioning stop portion, and positioning the inner branch portion between the outer branch portion, thereby juxtaposing the outer floss tensioning grooves and the inner floss tensioning grooves approximately on the same line.

Additionally, the floss moving means moves the floss by approximately parallel positioning the outer gripping portion and the inner gripping portion with a space portion being provided in vertical direction, interposing a movement supporting point portion in the space portion, fixing a base of the outer gripping portion and a base of the inner gripping portion by a rotatable fixing portion, pivotally fitting a pivot floss moving portion having on its upper surface a moving button and a pawl portion for the floss onto a pivot shaft, engaging the floss with the pawl portion for the floss of the pivot floss moving portion, and pivoting the moving button.

By tensioning the floss in double and providing the floss moving means for moving the floss, the movable dental floss according to the invention makes it possible to simultaneously clean the interdentium and the tooth surface. Further, by juxtaposing the outer floss tensioning grooves and the inner floss tensioning grooves of the floss tensioning means approximately on the same line, it makes it possible to effectively clean the teeth. Additionally, by providing the floss moving means, it makes it possible to simultaneously clean the interdentium and the tooth surface.

BRIEF DESCRIPTION OF THE DRAWINGS

Drawings of the invention are described.

Figure 1:
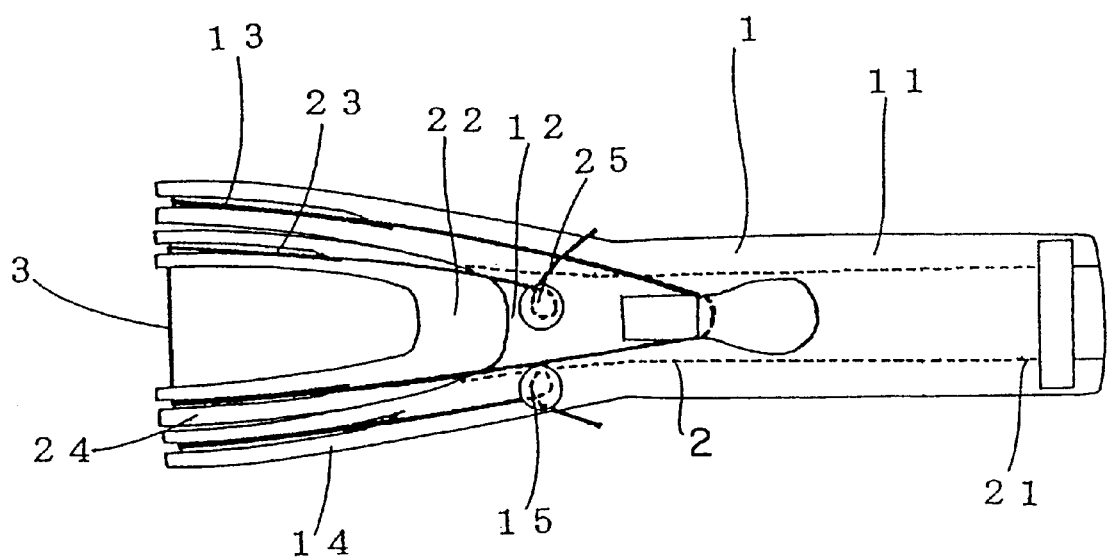
FIG. 1 is a plan view of an embodiment of a movable dental floss according to the invention under a state that the floss is tensioned.

1 is an outer floss tensioning member, 11 an outer gripping portion, 12 an outer branch portion, 13 an outer floss tensioning groove, 14 an outer floss tensioning lever, 15 an outer floss tensioning stop portion, 2 an inner floss tensioning member, 21 an inner gripping portion, 22 an inner branch portion, 23 an inner floss tensioning groove, 24 an inner floss tensioning lever, 25 an inner floss tensioning stop portion, 26 a convex portion, 3 a floss, 4 a space portion, 5 a movement supporting point portion, 6 a fixing portion, 7 a pivot floss moving portion, 71 a moving button, 72 a pawl portion for the floss, 73 a pivot shaft, and 74 a base portion.

DETAILED DESCRIPTION OF THE INVENTION

The present invention relates to a movable dental floss which can suitably remove food pieces, etc. lodged in an interdentium between teeth or a gap between a tooth and the gingiva portion thereof without injuring the gingiva portion, etc., which expels periodontitis bacteria in a periodontal pocket and, moreover, which can be easily and simply used by any person.

The movable dental floss comprises an outer floss tensioning member 1 and an inner floss tensioning member 2 respectively having floss tensioning means at their tip sides, an outer gripping portion 11 and an inner gripping portion 21 provided at base end sides of the outer floss tensioning member 1 and the inner floss tensioning member 2, and floss moving means for tensioning a floss 3 in double by superposing the outer floss tensioning member 1 and the inner floss tensioning member 2 and for moving the floss 3.

Further, the floss tensioning means is constituted by providing the outer floss tensioning member 1 and the inner floss tensioning member 2 respectively with an outer branch portion 12 and an inner branch portion 22, respectively extending at tip end sides of the outer branch portion 12 and the inner branch portion 22 one pair of outer floss tensioning levers 14 each having an outer floss tensioning groove 13 and one pair of inner floss tensioning levers 24 each having an inner floss tensioning groove 23, providing an outer floss tensioning stop portion 15 and an inner floss tensioning stop portion 25 on each of upper surfaces of the outer gripping portion 11 and the inner gripping portion 21, tensioning between the outer floss tensioning grooves 13 and the inner floss tensioning grooves 23 the floss 3 whose both ends are stopped on the outer floss tensioning stop portion 15 and the inner floss tensioning stop portion 25, and positioning the inner branch portion 22 between the outer branch potion 12, thereby juxtaposing the outer floss tensioning grooves 13 and the inner floss tensioning grooves 23 approximately on the same line.

Additionally, the floss moving means moves the floss 3 by approximately parallel positioning the outer gripping portion 11 and the inner gripping portion 21 with a space portion 4 being provided in vertical direction, interposing a movement supporting point portion 5 in the space portion 4, fixing a base of the outer gripping portion 11 and a base of the inner gripping portion 21 by a rotatable fixing portion 6, pivotally fitting a pivot floss moving portion 7 having on its upper surface a moving button 71 and a pawl portion 72 for the floss onto a pivot shaft 73, engaging the floss 3 with the pawl portion 72 for the floss of the pivot floss moving portion 7, and pivoting the moving button 71.

That is, in an embodiment, the outer floss tensioning member 1 of the movable dental floss according to the invention is formed in an approximately Y-shape. At its base end side there is formed the outer gripping portion 11 for gripping with hand, and near at its middle there is provided the outer branch portion 12. Moreover, it has one pair of outer floss tensioning levers 14 extended from the outer branch portion 12 toward its tip end side and the floss tensioning grooves 13 provided at tips of the respective outer floss tensioning levers 14. And it is integrally formed of a plastics material having elasticity as a material property such as nylon or polyethylene or polypropylene, or a metal such as stainless steel. In the vicinity of the outer branch portion 12 of an upper surface of the outer floss tensioning member 1, there is provided the outer floss tensioning stop portion 15 for stopping the floss 3 mentioned later by winding its end portion thereon.

And, also the inner floss tensioning member 2 is similar to the outer floss tensioning member 1. At its base end side there is formed the inner gripping portion 21 for gripping with hand, and near at its middle there is provided the inner branch portion 22 with its width being made narrower than the outer branch portion 12. Moreover, it has one pair of inner floss tensioning levers 24 extended from the inner branch portion 22 toward its tip end side and the floss tensioning grooves 23 provided at tips of the respective inner floss tensioning levers 24. And it is integrally formed of a plastics material such as nylon or polyethylene or polypropylene, or a metal such as stainless steel. On an upper surface of the inner floss tensioning member 2, there is provided the inner floss tensioning stop portion 25 for stopping the floss 3 by winding its end portion thereon.

Further, the floss 3 is generally referred to as thread toothpick and is a thread-like one made of vegetable fibers or synthetic resin fibers.

Next, the outer gripping portion 11 of the outer floss tensioning member 1 and the inner gripping portion 21 of the inner floss tensioning member 2 are positioned approximately parallel in vertical direction with the space portion 4 of some width provided. The movement supporting point portion 5 is interposed in the space portion 4 by an elastic force of the inner gripping portion 21. A tip of the movement supporting point portion 5 becomes a supporting point when the floss 3 is moved, and it is fixed to a lower surface of the outer gripping portion 11 or an upper surface of the inner gripping portion 21, or is protruded therefrom.

Figure 2:
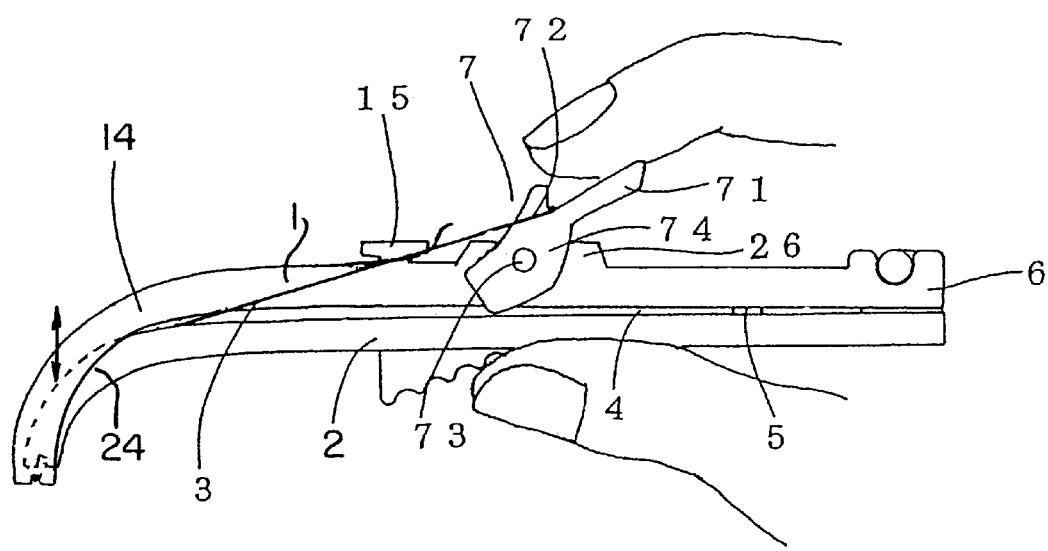
FIG. 2 is a schematic side view for explaining the embodiment of the movable dental floss according to the invention.
Figure 3:
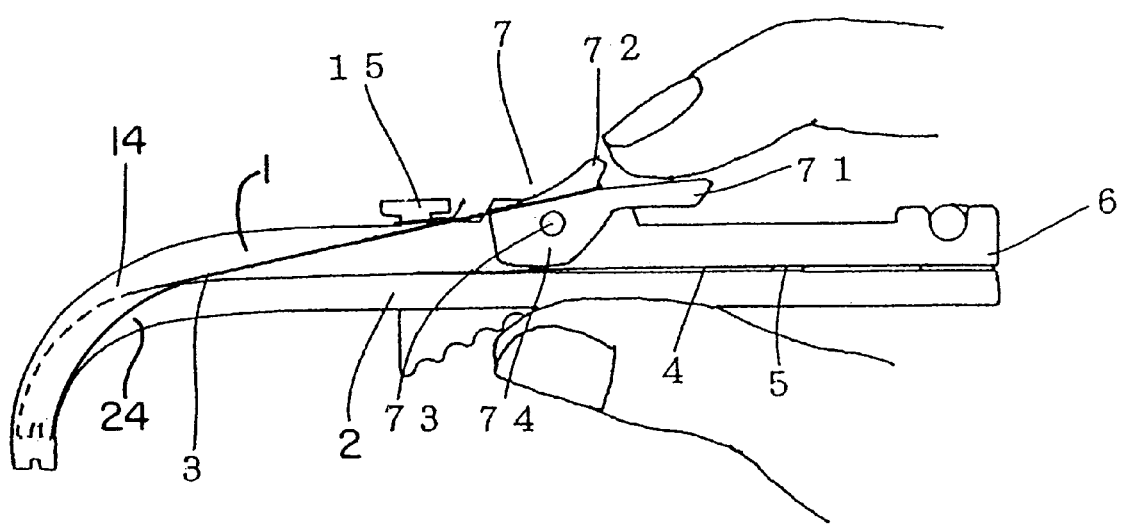
FIG. 3 is a schematic side view showing the movable dental floss according to the invention when it is moved.

Further, the respective base ends of the outer gripping portion 11 and the inner gripping portion 21 are fixed by the rotatable fixing portion 6. As shown in FIG. 2 and FIG. 3, in the embodiment it is made rotatable by protruding it to the space portion 4 of the base ends between the lower surface of the outer gripping portion 11 and the upper surface of the inner gripping portion 21 in a semicircular manner, providing through holes in the respective semicircles, and inserting a pin into the through holes.

Next, the movable dental floss according to the invention is provided with the pivot floss moving portion 7 for moving the floss 3 by pivoting the inner gripping portion 21 on the upper surface. As shown in the drawings, in the embodiment the plate-like convex portion 26 is protruded on the outer gripping portion 11. The base portion 74 of the pivot floss moving portion 7 formed so as to stride over the convex portion 26 is formed, and it is made pivot able by inserting the pivot shaft 73 through the convex portion 26 and the base portion 74. The pawl portion 72 for the floss for engaging with the floss 3 is formed on an upper surface of the pivot floss moving portion 7, and the moving button 71 is protruded in a base end direction for moving the pivot floss moving portion 7 to be pivoted with a fingertip.

Figure 4:
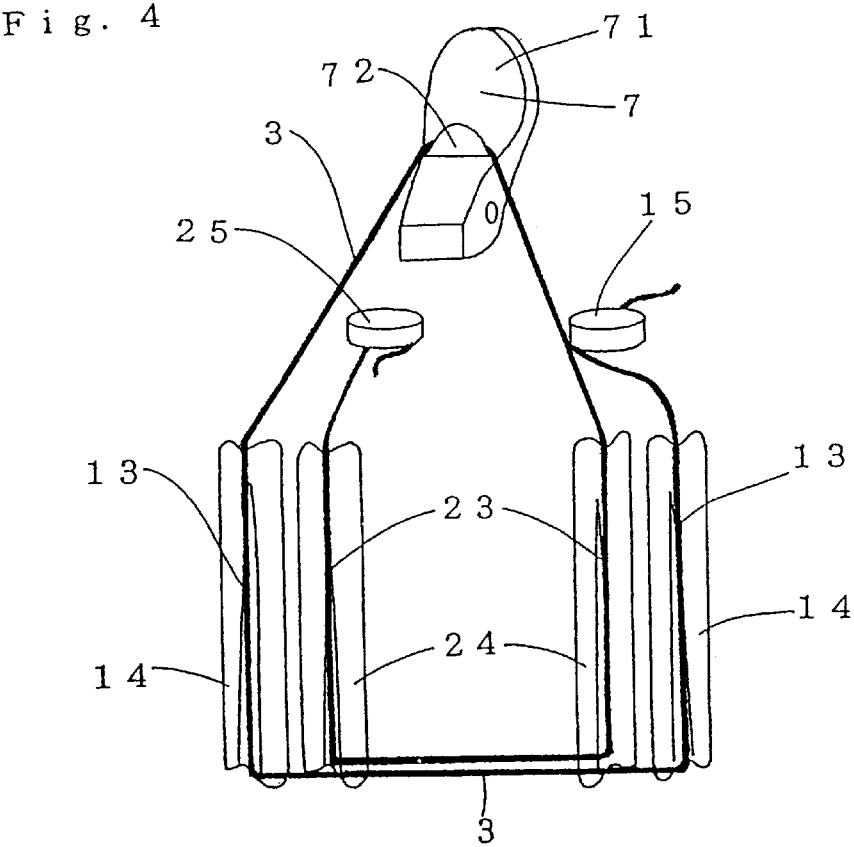
FIG. 4 is an explanatory view for a main section of the movable dental floss according to the invention.
Figure 5:
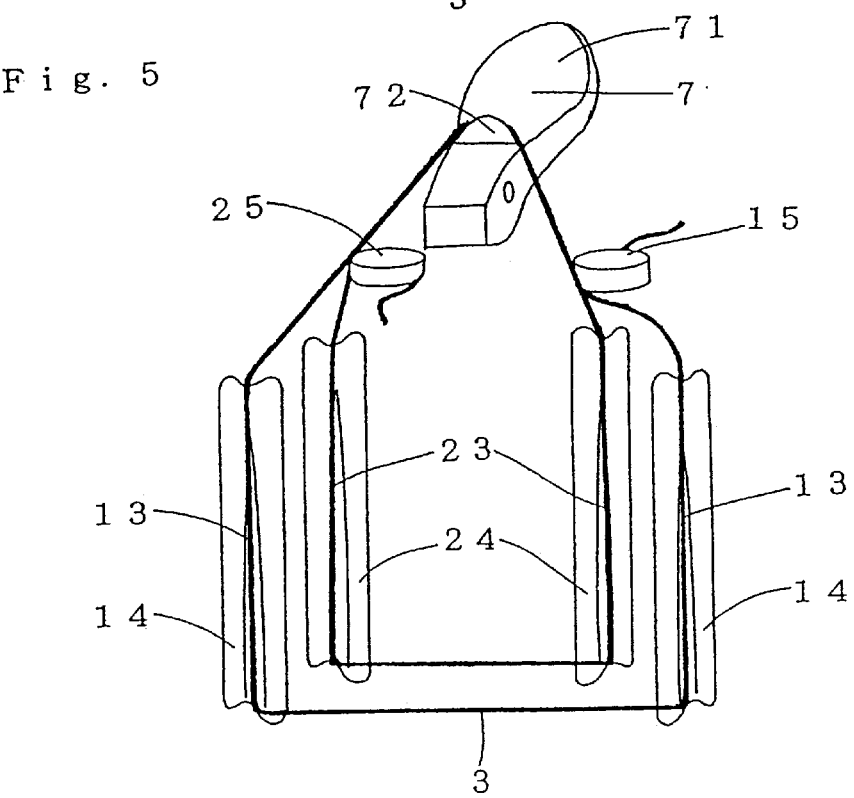
FIG. 5 is an explanatory view for the main section, showing the movable dental floss according to the invention when it is moved.

And, as shown in FIG. 4 and FIG. 5, in the floss tensioning means, end portions of the floss 3 are respectively stopped on the outer floss tensioning stop portion 15 and the inner floss tensioning stop portion 25. That is, one end side of the floss 3 is extended from the outer floss tensioning stop portion 15 to the respective outer floss tensioning grooves 13·13, the other end side of the floss 3 from the inner floss tensioning stop portion 25 to the respective inner floss tensioning grooves 23·23, and an approximately central part of the floss 3 is engaged with the pawl portion 72 for the floss of the pivot floss moving portion 7.

That is, when the movable dental floss according to the invention is gripped and the moving button 71 of the pivot floss moving portion 7 constituting the floss moving means is moved by a fingertip, the extended floss 3 is tensioned, so that the floss 3 extended between the respective outer floss tensioning grooves 13·13 and between the respective inner floss tensioning grooves 23·23 is moved in vertical direction and horizontal direction.

Further, by additionally providing the moving button 71 with moving means moved with a vibration element electrically actuated or a motor, it can be moved by an electrical motion as well.

Moreover, in the movable dental floss according to the invention, the inner branch portion 22 is positioned between the outer branch portion 12. That is, in case where the inner floss tensioning member 2 is moved by moving the pivot floss moving portion 7, it is formed such that the one pair of outer floss tensioning levers 14·14 don't contact with the one pair of inner floss tensioning levers 24·24.

And, the outer floss tensioning grooves 13·13 provided at the tips of the one pair of outer floss tensioning levers 14·14 and the inner floss tensioning grooves 23·23 provided at the tips of the one pair of inner floss tensioning levers 24·24 are juxtaposed approximately on the same line. That is, by changing lengths and degrees of curve of the outer floss tensioning levers 14·14 and the inner floss tensioning levers 24·24, the double floss 3 to be tensioned is tensioned approximately on the same line.

Next, the moving button 71 of the pivot floss moving portion 7 provided above is moved with a fingertip by gripping the outer gripping portion 11 and the inner gripping portion 21 and, as a result, the outer floss tensioning levers 14·14 or the inner floss tensioning levers 24·24 are moved in vertical direction and horizontal direction, so that the floss 3 tensioned at the tips is also moved in vertical direction and horizontal direction at a vicinity of the gingiva.

Figure 6:
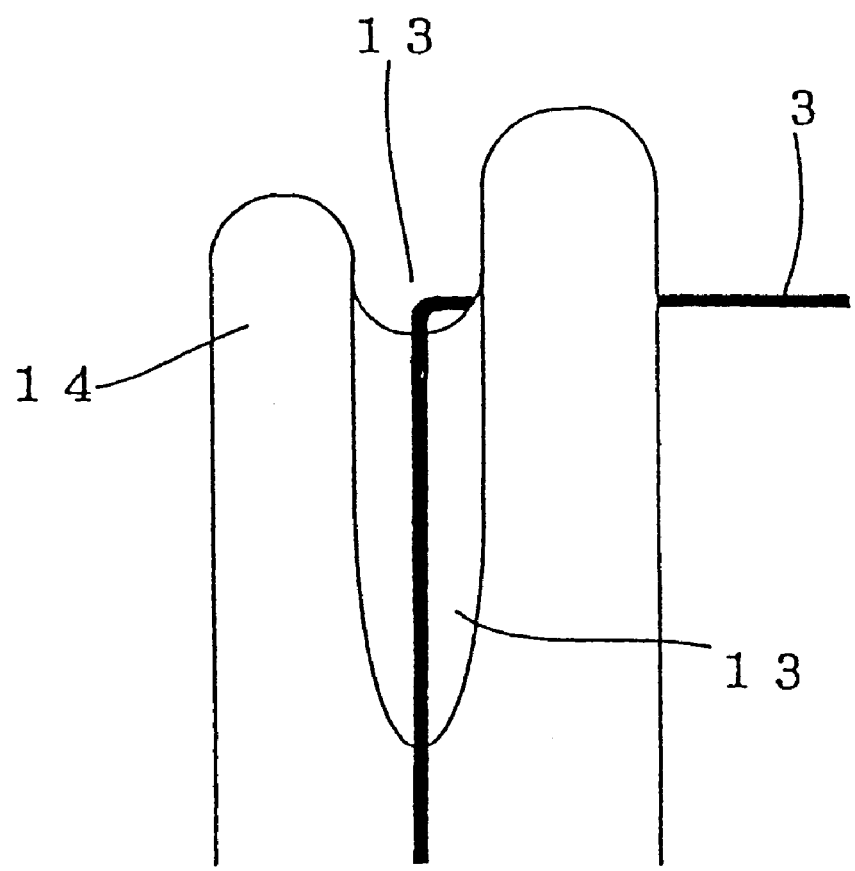
FIG. 6 is an explanatory view representing a floss tensioning groove at a tip of the embodiment of the movable dental floss according to the invention.

And, as shown in FIG. 6, by the fact that the respective floss tensioning grooves 13·13 and 23·23 for extending the floss 3 are provided along a longitudinal direction on upper surfaces of the respective floss tensioning levers 14·14 and 24·24, the floss 3 whose both ends are stopped on the outer floss tensioning stop portion 15 and the inner floss tensioning stop portion 25 can be easily tensioned.

Therefore, in the invention, an elasticity of the material property is utilized and the double floss juxtaposed approximately on the same line is vertically and horizontally moved by moving the moving button of the floss moving means with a fingertip to thereby abut it against a whole of the teeth, so that it is possible to remove the food pieces, remove the food pieces in the interdentium and expel the periodontitis bacteria from the periodontal pocket and, further, a movement of the floss performed hitherto by a feel of fingers or arms can be automatically or semiautomatically performed, thereby bringing about very significant advantages.

What is claimed is:

1. A movable dental floss comprising an outer floss tensioning member and an inner floss tensioning member respectively having floss tensioning means at their tip sides, an outer gripping portion and an inner gripping portion provided at base end sides of the outer floss tensioning member and the inner floss tensioning member, and floss moving means for tensioning a floss in double by superposing the outer floss tensioning member and the inner floss tensioning member and for moving the floss;

wherein the floss tensioning means is constituted by providing the outer floss tensioning member and the inner floss tensioning member respectively with an outer branch portion and inner branch portion, respectively extending at tip end sides of the outer branch portion and the inner branch portion one pair of outer floss tensioning levers each having an outer floss tensioning groove and one pair of inner floss tensioning levers each having an inner floss tensioning groove, providing an outer floss tensioning stop portion and an inner floss tensioning stop portion on each of upper surfaces of the outer gripping portion and the inner gripping portion, tensioning between the outer floss tensioning grooves and the inner floss tensioning grooves the gloss whose both ends are stopped on the outer floss tensioning stop portion and the inner floss tensioning stop portion, and positioning the inner branch portion between the outer branch portion, thereby juxtaposing the outer floss tensioning grooves and the inner floss tensioning grooves approximately on the same line; and wherein the floss moving means moves the floss by approximately parallel positioning the outer gripping portion and the inner gripping portion with a space portion and the inner gripping portion with a space portion being provided in vertical direction, interposing a movement supporting point portion in the space portion, fixing a base of the outer gripping portion and a base of the inner gripping portion by a rotatable fixing portion, pivotally fitting a pivot floss moving portion having on its upper surface a moving button and a pawl button for the floss onto a pivot shaft, engaging the floss with the pawl portion for the floss of the pivot floss moving portion, and pivoting the moving button.

2. A movable dental floss comprising an outer floss tensioning member and an inner floss tensioning member;

said outer floss tensioning member and said inner floss tensioning member each including
a pair of tensioning levers which face each other,
a branch portion from which said pair of tensioning levers extend,
a gripping portion which extends from said branch portion in a direction opposite to the extension direction of the tensioning levers,
a floss tensioning stop portion to which an end of floss is secured, and
each pair of tensioning levers of said outer floss tensioning member and said inner floss tensioning member having a tip end formed with a floss tensioning groove for receiving the floss therein;

said pair of tensioning levers of said inner floss tensioning member being disposed between said pair of tensioning levers of said outer floss tensioning member; and said gripping portion of said outer floss tensioning member having a base end which is connected by a rotatable fixing portion to a base end of said gripping portion of said inner floss tensioning member so that said pair of tensioning levers of said inner floss tensioning member is swingable between and relative to said pair of tensioning levers of said outer floss tensioning member.

3. A movable dental floss according to claim 2, wherein at least said pair of tensioning levers of said inner floss tensioning member is swingable between and relative to said pair of tensioning levers said outer floss tensioning member in a direction of a height of teeth.

4. A movable dental floss according to claim 2, wherein both said pair of tensioning levers of said outer floss tensioning member and said pair of tensioning levers of said inner floss tensioning member are curved more in a direction of movement of one of said pairs of tensioning levers relative to the other of said pairs of tensioning levers at positions farther than the respective branch portion so not to interfere with teeth when said one of said pairs of tensioning levers is moved relative to said other of said pairs of tensioning levers in a direction of a height of the teeth.

5. A movable dental floss according to claim 4, in which one of said gripping portions of said outer floss tensioning member has a supporting point portion which protrudes toward another gripping portion and said another gripping portion has a portion which is brought into contact with said supporting point portion and is resiliently deformed thereby to allow said pair of tensioning levers of said inner floss tensioning member to swing between and relative to said pair of tensioning levers of said outer floss tensioning member.

6. A movable dental floss according to claim 4, wherein one of said gripping portions of said outer floss tensioning member and said inner floss tensioning member has a pawl portion for receiving a floss and a floss moving member which is adapted to move when operated to pull the floss which extends along said tensioning lever for allowing said one of said tensioning levers to swing.

7. A movable dental floss according to claim 5, wherein one of said gripping portions of said outer floss tensioning member and said inner floss tensioning member has a pawl portion for receiving a floss and a floss moving member which is adapted to move when operated to pull the floss which extends along said tensioning lever for allowing said one of said tensioning levers to swing.

\* \* \* \* \*